US010040729B2

(12) United States Patent
Kim et al.

(10) Patent No.: US 10,040,729 B2
(45) Date of Patent: Aug. 7, 2018

(54) GROWTH SUPPLEMENT FOR EFFICIENT PRODUCTION OF AGRICULTURAL AND LIVESTOCK PRODUCTS

(71) Applicant: WIZBIO CO., Ltd., Seoul (KR)

(72) Inventors: Yong Guk Kim, Daejeon (KR); Jae Sung Park, Daejeon (KR); Tae Hyoun Kim, Chungcheongnam-do (KR)

(73) Assignee: WIZBIO CO., Ltd., Seoul (KR)

( * ) Notice: Subject to any disclaimer, the term of this patent is extended or adjusted under 35 U.S.C. 154(b) by 25 days.

(21) Appl. No.: 14/772,258

(22) PCT Filed: Aug. 30, 2013

(86) PCT No.: PCT/KR2013/007796
§ 371 (c)(1),
(2) Date: Sep. 2, 2015

(87) PCT Pub. No.: WO2014/051266
PCT Pub. Date: Apr. 3, 2014

(65) Prior Publication Data
US 2016/0031763 A1 Feb. 4, 2016

(30) Foreign Application Priority Data
Sep. 28, 2012 (KR) .................. 10-2012-0108703

(51) Int. Cl.
| | |
|---|---|
| *C05D 3/02* | (2006.01) |
| *C05D 5/00* | (2006.01) |
| *C05D 1/00* | (2006.01) |
| *C05D 9/02* | (2006.01) |
| *A23K 20/24* | (2016.01) |

(Continued)

(52) U.S. Cl.
CPC .............. *C05D 1/00* (2013.01); *A01N 43/16* (2013.01); *A01N 59/00* (2013.01); *A01N 59/08* (2013.01); *A01N 65/08* (2013.01); *A01N 65/12* (2013.01); *A01N 65/16* (2013.01); *A01N 65/42* (2013.01); *A23K 20/163* (2016.05); *A23K 20/20* (2016.05); *A23K 20/24* (2016.05); *A23K 40/20* (2016.05); *A23K 40/25* (2016.05); *A61K 31/70* (2013.01); *A61K 31/7004* (2013.01); *A61K 33/10* (2013.01); *A61K 33/14* (2013.01); *A61K 36/185* (2013.01); *A61K 36/258* (2013.01); *A61K 36/288* (2013.01); *A61K 36/45* (2013.01); *A61K 36/725* (2013.01); *A61K 36/736* (2013.01); *A61K 36/79* (2013.01); *A61K 36/8962* (2013.01); *A61K 47/02* (2013.01); *A61K 47/26* (2013.01); *C05D 3/00* (2013.01); *C05D 3/02* (2013.01); *C05D 5/00* (2013.01); *C05D 9/02* (2013.01); *C05F 5/00* (2013.01); *C05F 11/00* (2013.01); *C05F 11/08* (2013.01); *C05G 3/02* (2013.01); *Y02A 40/209* (2018.01)

(58) Field of Classification Search
CPC ... C05D 1/00; C05D 9/02; C05D 3/00; C05D 5/00; C05D 3/02; C05G 3/02; A61K 36/79; A61K 36/288; A61K 36/258; A61K 47/26; A61K 36/736; A61K 36/45; A61K 47/02; A61K 36/185; A61K 31/70; A61K 36/8962; A61K 36/725; A61K 33/14; A61K 31/7004; A61K 33/10; A23K 1/1643; A23K 1/175; A23K 20/24; A23K 40/25; A23K 40/20; A23K 20/163; A23K 20/20; C05F 5/00; C05F 11/08; C05F 11/00; Y02A 40/209; A01N 59/08; A01N 65/12; A01N 59/00; A01N 43/16; A01N 65/08; A01N 65/42; A01N 65/16
See application file for complete search history.

(56) References Cited

U.S. PATENT DOCUMENTS

| | | | | |
|---|---|---|---|---|
| 4,942,042 A | * | 7/1990 | Bhargava | A61K 33/14 424/679 |
| 5,038,396 A | * | 8/1991 | Gjerlov | A61K 36/68 424/601 |
| 5,728,675 A | * | 3/1998 | Schaefer | A23K 1/1631 514/21.92 |

FOREIGN PATENT DOCUMENTS

| | | |
|---|---|---|
| JP | 2008-017795 A | 1/2008 |
| KR | 10-0374084 B1 | 5/2003 |

(Continued)

OTHER PUBLICATIONS

Nakanishi, K., JP 2007082513 A, Fermented Liquor for use as antimicrobial comprises fermented Japanese apricot seasoning liquid, Apr. 2007, Derwent Abstract, Derwent-Acc-No. 2007-337363, pp. 1-4.*

(Continued)

*Primary Examiner* — John Pak
*Assistant Examiner* — Andriae M Holt
(74) *Attorney, Agent, or Firm* — Revolution IP, PLLC

(57) ABSTRACT

Provided is a growth supplement for efficient production of agricultural and livestock products, more specifically, a growth supplement for environment-friendly crop cultivation and livestock rearing to increase yields of crops and livestock, which is prepared by mixing specific amounts of antibiotic fruit juices, one or more sources of sugar, one or more sources of hydrogen carbonate, one or more sources of chloride ion and antifebrile vegetable juices depending on crops (species) and cultivation (livestock) conditions to feed the livestock or crops. The growth supplement is prepared by admixing and stirring antibiotic fruit juices in an amount of 2 to 10 parts by weight; the source of hydrogen carbonates in an amount of 1 to 4 parts by weight; the source of chloride ion in an amount of 1 to 4 parts by weight; and antifebrile vegetable juices in an amount of 2 to 8 parts by weight, based on 100 parts by the source of sugar.

6 Claims, 4 Drawing Sheets

(51) Int. Cl.

| | |
|---|---|
| *A61K 31/7004* | (2006.01) |
| *A61K 36/79* | (2006.01) |
| *A61K 36/258* | (2006.01) |
| *A61K 36/288* | (2006.01) |
| *A61K 36/45* | (2006.01) |
| *A61K 36/8962* | (2006.01) |
| *A61K 36/725* | (2006.01) |
| *A61K 47/02* | (2006.01) |
| *A61K 47/26* | (2006.01) |
| *A61K 33/10* | (2006.01) |
| *A61K 33/14* | (2006.01) |
| *A01N 43/16* | (2006.01) |
| *A01N 59/00* | (2006.01) |
| *A01N 59/08* | (2006.01) |
| *A01N 65/08* | (2009.01) |
| *A01N 65/16* | (2009.01) |
| *A01N 65/42* | (2009.01) |
| *A01N 65/12* | (2009.01) |
| *A23K 40/25* | (2016.01) |
| *A23K 40/20* | (2016.01) |
| *A61K 31/70* | (2006.01) |
| *C05F 11/00* | (2006.01) |
| *C05F 11/08* | (2006.01) |
| *C05D 3/00* | (2006.01) |
| *C05F 5/00* | (2006.01) |
| *A61K 36/185* | (2006.01) |
| *A61K 36/736* | (2006.01) |
| *C05G 3/02* | (2006.01) |
| *A23K 20/163* | (2016.01) |
| *A23K 20/20* | (2016.01) |

(56) References Cited

FOREIGN PATENT DOCUMENTS

| | | |
|---|---|---|
| KR | 10-0748716 B1 | 8/2007 |
| KR | 10-2011-0047350 A | 5/2011 |

OTHER PUBLICATIONS

International Search Report for PCT/KR2013/007796.

\* cited by examiner

GROWTH SUPPLEMENT FOR EFFICIENT PRODUCTION OF AGRICULTURAL AND LIVESTOCK PRODUCTS

FIELD OF THE INVENTION

The present invention relates to a growth supplement for efficient production of agricultural and livestock products, more specifically, a growth supplement for environment-friendly crop cultivation and livestock rearing to increase yields of crops and livestock, which is prepared by mixing specific amounts of antibiotic fruit juices, one or more sources of sugar, one or more sources of hydrogen carbonate, one or more sources of chloride ion and antifebrile vegetable juices depending on crops (species) and cultivation (livestock) conditions to feed the livestock or crops.

BACKGROUND OF THE INVENTION

Generally, the use of chemical fertilizers and agricultural pesticides has been continuously increased to increase agricultural production output; however, it also had dangerous impacts on the ecosystem by causing soil acidification, soil depletion, soil and water contamination, and the like. In order to resolve such problems, efforts have been made by the Korean government to place more importance on environment-friendly crops by launching a policy which reduces 40% of chemical fertilizers and agricultural pesticides usage by 2013. Also, in private sector, environment-friendly agriculture techniques, such as organic farming, soil fertility improvement technologies, etc., have been developed and practiced, thereby heeding the growing demands of safe agricultural products by the consumers, and thus, eventually contributing to an increase in income of farmers.

Despite efforts made by the government and the private sector, most of the farmers are small-scale farmers who make a living by selling what they harvest from their small lands, and thus an indiscriminate use of livestock manure and compost to increase production are prevalent and over-exploitation of natural resources in soil are continued. Such trends had caused salinization and replant failure in many areas, and caused great difficulties to many farmers. As a part of a solution to this problem, an effective method is suggested to promote plant growth by assisting photosynthesis without relying on chemical fertilizers or relentlessly using organic matters.

Meanwhile, similar to the field of agriculture, synthetic antibiotics such as penicillin, bacitracin and the like have been widely used as a feed additive since 1950s to promote growth of young livestock, as well as to improve feedstuff efficiency and production efficiency of livestock product.

Generally, the mechanism of action of antibiotics is known to promote growth of young livestock by eliminating pathogenic bacteria in the intestines, e.g., *Salmonella, E. coli, Clostridium*, etc., by destroying their cell walls, and thinning intestinal absorptive cells of the small intestine in livestock to increase the nutrient absorption rate.

Several issues have been brought up regarding the use of antibiotics including antibiotic accumulation possibilities, adverse side effects on body's immune system when ingested by human, and the like. Nowadays, people are becoming health-conscious and, as a result, their concerns over adverse side effects of antibiotics on body's immune system due to indiscriminate use of antibiotics caused their preferences of livestock products to shift from quantity to quality. Accordingly, there is a trend of prohibiting or restricting the use of synthetic antibiotics to livestock in some countries centering on European countries including Sweden, etc. Thus, there is a growing demand for an alternative to synthetic antibiotics; and research and development of safe candidate materials and effectiveness study thereof still remain as an issue needs to be addressed in the livestock industry.

SUMMARY OF THE INVENTION

The present invention seeks to redress the above-mentioned problems by providing a growth supplement based on well-balanced, environment-friendly materials to promote healthy development and growth of crops and livestock.

The growth supplement in accordance with the present invention comprises antibiotic fruit juices, one or more sources of sugar, one or more sources of hydrogen carbonate, one or more sources of chloride ion and antifebrile vegetable juices.

The said growth supplement is prepared by admixing and stirring antibiotic fruit juices in an amount of 2 to 10 parts by weight; one or more sources of hydrogen carbonate in an amount of 1 to 4 parts by weight; one or more sources of chloride ion in an amount of 1 to 4 parts by weight; and antifebrile vegetable juices in an amount of 2 to 8 parts by weight, based on 100 parts by one or more sources of sugar.

Meanwhile, the antibiotic fruit juices may be one or more selected from the group consisting of Japanese apricot, schizandra fruit, jujube, red ginseng and blueberry.

Further, the source of sugar may be one or more selected from the group consisting of glucose, brown sugar and oligosaccharide; the source of hydrogen carbonate may be one or more selected from the group consisting of sodium hydrogen carbonate and potassium hydrogen carbonate; the source of chloride ion may be one or more selected from the group consisting of sodium chloride, potassium chloride, magnesium chloride and calcium chloride; and the antifebrile vegetable juices may be one or more selected from the group consisting of onion juice and dandelion juice.

The growth supplement in accordance with the present invention is prepared by diluting with water or adding to feedstuff.

According to the composition as described above, immune responses in crops and livestock can be improved due to the presence of antibiotic fruit juices; metabolism, e.g., respiration, can be increased owing to the presence of sugar; and therefore, weight gain in livestock as well as crop productivity can be significantly enhanced.

Further, the presence of hydrogen carbonate and chloride ion can strengthen biological circuit and, in the case of livestock, antifebrile vegetable juices can give antifebrile effects, so that animals can maintain their biological functions well, even under stressful conditions including disease, excessively high temperatures during summer, etc.

Further, fruit juices of Japanese apricot, schizandra fruit, jujube, red ginseng and blueberry are used as a natural antibiotic fruit juice to replace synthetic antibiotics and enhance anti-oxidative activity and immune response such as antibiotic activity in vivo to yield high-quality crops and livestock products.

Further, the present invention supplies carbohydrates such as glucose, brown sugar and oligosaccharide, and thus increases productivity of crops and livestock by enhancing crop yield and promoting weight gain of livestock. In the case of plants, the present invention provides glucose to make up any shortfall from photosynthesis. In the case of livestock, the present invention supplies glucose, the final product in carbohydrate digestion, which can be absorbed directly without going through unnecessary digestive processes to accelerate Tricarboxylic Acid Cycle (TCA cycle), the respiratory metabolism. Also, brown sugar can be used as secondary source of glucose, which can be converted into glucose as it passes through the digestive system, so that it may replenishe sugar to relieve sugar shortage, and thereby preventing undesirable proteolysis. In the case of plants, fast absorption of sugar into the plants can be allowed by supplying brown sugar, because carbohydrates in plants are transported in the form of sugar.

Further, hydrogen carbonate such as sodium bicarbonate, potassium bicarbonate is used in the present invention as a chemical buffer for the biological circuit. As such, hydrogen carbonate supplies electrolytes and hydrogen ion ($H^+$) in the body and regulates acid-base balance by mediating bicarbonate buffer system to maintain the biological circuit, and thereby allowing production of healthy crops and livestock.

Further, the present invention employs chloride ion including sodium chloride, potassium chloride, magnesium chloride and calcium chloride for electrical balance as well as to provide positively charged ions ($Na^+$, $K^+$, $Ca^{2+}$, $Mg^{2+}$, etc) and negatively charged ions ($Cl^-$), which are essential elements for the extracellular fluid, to maintain electrical balance in the body. Furthermore, the present invention develops a secondary defense mechanism against a sudden change in pH to prevent acidosis and alkalosis, thereby protecting the biological circuit.

Further, the present invention uses natural antifebrile vegetable juices including onion juice and dandelion juice to lower excessive body heat, which not only lowers body heat generated as a result of metabolism but also prevents the reduction in growth rate caused by loss of appetite in animals during summer. Moreover, the growth supplement in accordance with the present invention activates metabolism in animals, which creates a large amount of heat by APT generation from TCA cycle, to promote antifebrile activity, and thus allowing promotion of health and weight gain caused by good appetite, and ultimately allowing efficient production of agricultural and livestock products.

BEST MODE FOR CARRYING OUT THE INVENTION

Hereinafter, a preferred embodiment in accordance with the present invention is described in detail with reference to the attached figures.

The term "comprise," as used herein, refers are inclusive or open-ended and do not exclude additional, unrecited elements or method steps.

The growth supplement in accordance with the present invention, which is organically composed on functionality, employs antibiotic fruit juices to enhance immune responses in crops and livestock, and sugars to promote weight gain owing to increased metabolism, e.g., respiration. Further, the presence of hydrogen carbonate and chloride ion can strengthen biological circuit and, in the case of livestock, antifebrile vegetable juices provide antifebrile effects so that animals can maintain their biological functions well even under stressful conditions, such as disease, excessively high temperatures during summer, etc. Particularly, the ability to maintain balanced biological circuit is much more difficult in immature organisms than mature organisms, and thus a functional approach to healthy growth of crops and weight gaining in livestock at growth stage is very important. The present invention not only allows environment-friendly crop cultivation crops and livestock rearing to increase yields of crops and livestock, but also accelerates growth rate of plants, which reduces time require to grow vegetables, thereby allowing increased total production amount, and promotes weight gain in livestock; and therefore, the present invention allows efficient production of environment-friendly agricultural and livestock products on a large scale.

Figure 1:
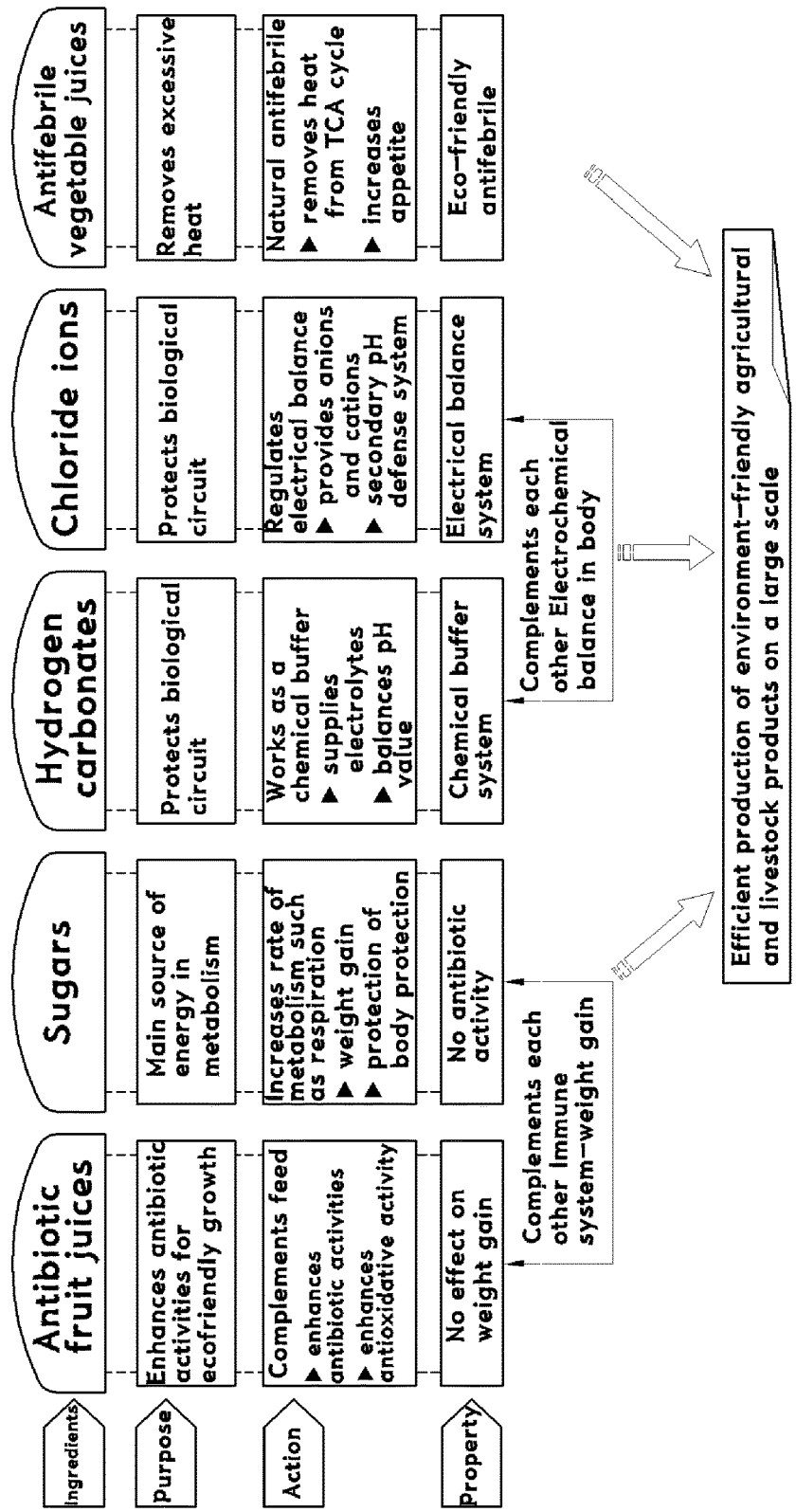
FIG. 1 is a block diagram demonstrating the functions of components which make up the growth supplement in accordance with one embodiment of the present invention.

In addition, with reference to FIG. 1, the growth supplement may be prepared in the form of liquid phase or solid phase. Particularly, in the case of small-sized animals such as poultry having relatively short digestion time as compared to large-sized animals, the liquid phase type features very fast body absorption rate, and thus, the liquid type growth supplement is preferred to poultry.

TABLE 1

| Category | Liquid phase | Solid phase | Note |
| --- | --- | --- | --- |
| Body absorption rate | Very fast | Fast | |
| Drinking water management | Required (diluted to water) | Not required | |
| Storage convenience | Average (can be improved by installing feeding equipment) | Easy (as compared to liquid phase) | |
| Target crops | Annual, perennial crops and fruit trees | N/A | |
| Target livestock species | Small, medium-large size livestock | | |

Table 1 is a comparison chart of the growth supplement in the form of liquid phase and solid phase.

The growth supplement according to one embodiment of the present invention comprising antibiotic fruit juices, sugars, hydrogen carbonates, chloride ions and antifebrile vegetable juices is prepared in the form of liquid phase.

The antibiotic fruit juice suppresses growth of pathogen, e.g., *Salmonella, Enterobacter, E. coli*, etc, in livestock, thereby making them healthy and energetic. Particularly, Japanese plum juice is known to be effective for improving metabolic activities such as antibiotic activities, fatigue recovery, increase in appetite, etc., and for recovering liver damages; and thus it has been widely used in oriental medicine as well as in folk therapy. The antibiotic fruit juices are alkaline and contain a large amount of organic acids such as citric acid, malic acid, succinic acid, etc.; and it has been reported that the antibiotic fruit juices promote physiological activities such as enhanced digestion, antibiotic activities, liver protection and the like. Once the growth supplement is ingested by livestock, it helps digestion and also can reduce bad odor of livestock excretions.

The antibiotic fruit juices contained in the growth supplement of the present invention comprises one or more plant materials selected from the group consisting of Japanese apricot, schizandra fruit, jujube, red ginseng and blueberry.

The source of sugar is a relatively good energy source, and can be directly used to supply energy needed for metabolism, e.g., respiration, and thus it is considered as an essential nutrient for homeostasis and growth in living organisms. Glucose, in particular, is produced via photosynthesis and used up in respiration in plants, so the present invention provides glucose to make up for any shortfall in plant respiration. In the case of livestock, glucose, the final product of carbohydrate digestion that can be absorbed directly in the small intestine without going through unnecessary digestive process, is used in the respiration and thus the rate of metabolism can be improved.

The source of sugar contained in the growth supplement of the present invention comprises one or more selected from the group consisting of glucose, brown sugar and oligosaccharide.

Preferably, the source of sugar is a mixture of glucose and brown sugar, and more preferably, the sugar is glucose only.

Meanwhile, the antibiotic fruit juices are preferably contained in an amount ranging from 2 to 10 parts by weight, based on 100 parts by weight of the source of sugar. As shown in FIG. 1, the antibiotic fruit juice enhances immune response and provides anti-oxidative activity but does not help in gaining weight; whereas sugar promotes weight gain and protects organs in the body. Therefore, the antibiotic fruit juice and the sugar are complementary to each other in their functions.

The hydrogen carbonates function as a chemical buffer to supply electrolytes and hydrogen ion ($H^+$) in the body, and also protects the biological circuit by triggering bicarbonate ($HCO_3^-$) buffer system to regulate acid-base balance, which is very important for survival of living organisms.

The source of hydrogen carbonate contained in the growth supplement of the present invention comprises one or more selected from the group consisting of sodium hydrogen carbonate, potassium hydrogen carbonate and calcium hydrogen carbonate.

Preferably, the source of hydrogen carbonate is sodium hydrogen carbonate.

The chloride ions provide positively charged ions ($Na^+$, $K^+$, $Ca^{2+}$, $Mg^{2+}$, etc) and negatively charged ions ($Cl^-$), which are essential elements for extracellular fluid, to maintain electrochemical balance in the body. In other words, the hydrogen carbonates and the chloride ions not only maintain acid-base balance, but also develop a secondary defense mechanism against a sudden change in pH caused by pulmonary or renal problem to prevent acidosis and alkalosis, thereby protecting the biological circuit.

The source of chloride ion contained in the growth supplement of the present invention comprises one or more selected from the group consisting of sodium chloride, potassium chloride, magnesium chloride and calcium chloride.

Preferably, the source of chloride ion is potassium chloride.

Meanwhile, the sources of the hydrogen carbonate and the chloride ion are preferably contained in an amount ranging from 1 to 4 parts by weight, based on 100 parts by weight of the source of sugar. As shown in FIG. 1, the hydrogen carbonates and chloride ions protect the biological circuit. The hydrogen carbonates maintain the chemical balance in the body; whereas the chloride ions regulate the electrical balance in the body. Therefore, the hydrogen carbonates and the chloride ions are complementary to balance electrochemical balance in the body.

In livestock husbandry, not only the heat generated in the bodies of livestock can cause serious problems, but also the loss of appetite caused by high temperature condition of livestock facilities during hot summer which causes a reduction in growth rate, and even a mass mortality. The present invention activates metabolism rate in animals, which creates a large amount of heat by APT generation from TCA cycle; and thus, it also comprises natural vegetable juices of dandelion and onion to promote antifebrile activity, and thus allowing promotion of health and weight gain caused by good appetite, and ultimately allowing efficient production of agricultural and livestock products.

The antifebrile vegetable juices in the growth supplement of the present invention comprise one or more selected from the group consisting of onion juice and dandelion juice.

Meanwhile, the antifebrile vegetable juices are preferably contained in an amount ranging from 2 to 8 parts by weight, based on 100 parts by weight of the sugar. As shown in FIG. 1, the antifebrile vegetable juices provide an antifebrile activity in an environment-friendly way to remove excessive heat from livestock.

Figure 2:
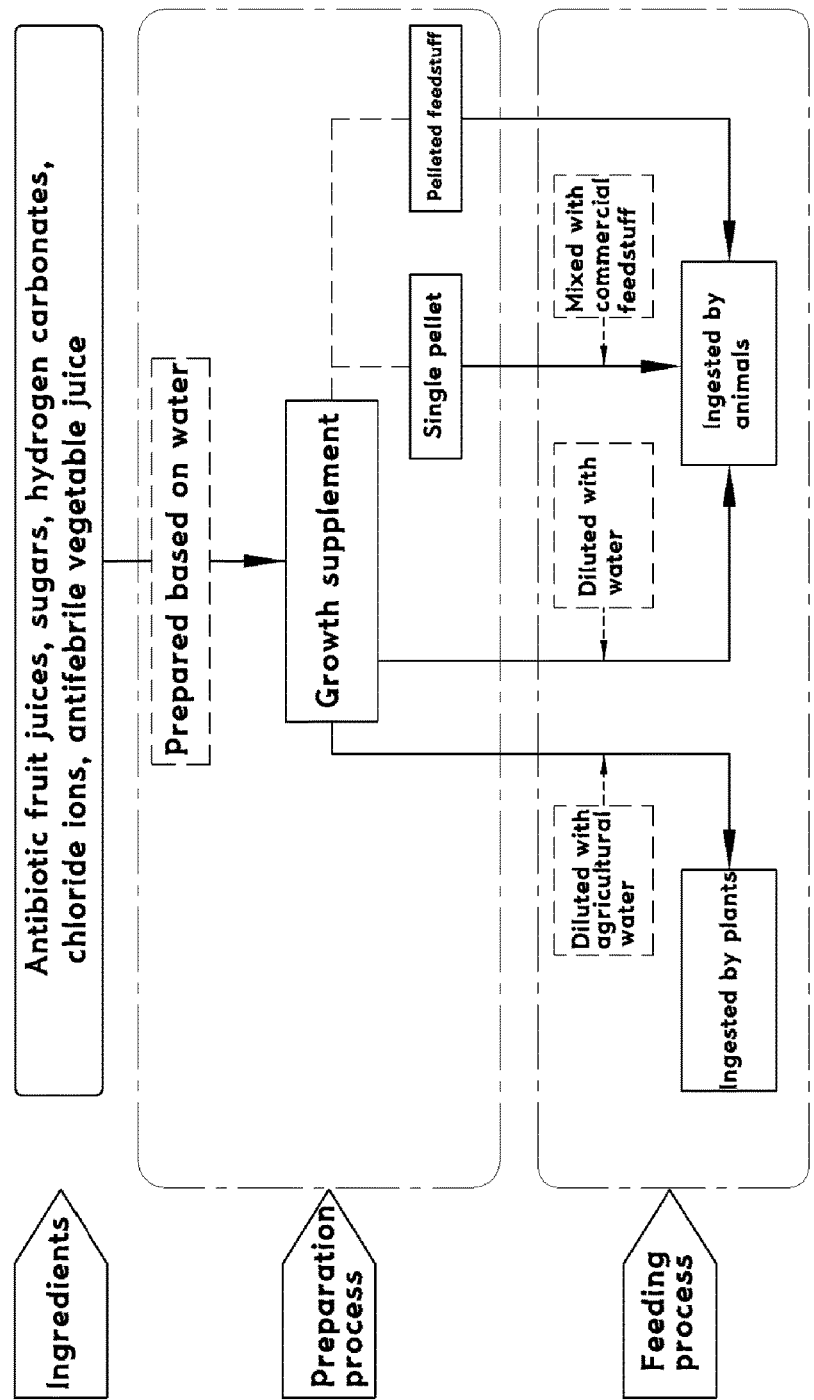
FIG. 2 is a diagram depicting the preparation process of the growth supplement in accordance with one embodiment of the present invention, and the feeding process to animals and plants.

The growth supplement in accordance with the present invention, with reference to FIG. 2, is prepared by diluting the antibiotic fruit juices, the source of sugar, the source of hydrogen carbonate, the source of chloride and the antifebrile vegetable juices as main functional ingredients with water, or mixing the main functional ingredients with feedstuff and then the mixture obtained is fed to livestock. If the growth supplement is prepared to feed plants, the main functional ingredients are diluted with agricultural water and then the mixture is fed to plants.

For example, the growth supplement in accordance with the present invention is diluted with water depending on the type of crop (species) and cultivation (livestock) conditions. If the growth supplement is prepared as single pellets, the growth supplement is mixed with a commercially available feedstuff. In the case of preparing pelleted or powdered feedstuff, the growth supplement is proportionally admixed with a commercially available feedstuff, and then fed to the subjects. When the growth supplement is used in the form of crude liquid, it is diluted with drinking water in a specific proportion. The growth supplement is diluted in an amount of 0.25 to 2.0 parts by weight, based on 100 parts by weight of agricultural water, and 0.33 to 1.5 parts by weight, based on 100 parts by weight of livestock drinking water for use in crops and livestock, respectively.

Hereinafter, the preparation of the growth supplement in accordance with an embodiment of the present invention is described in more detail with reference to the following Example.

EXAMPLE

First, in order to prepare a growth supplement, purified drinking water was boiled to increase solubility thereof, and then one or more sources of sugar and one or more sources of chloride ion added thereto, followed by stirring to completely dissolve in water. Subsequently, one or more sources of hydrogen carbonate was completely dissolved in the solution at a temperature ranging from 10 to 40° C. for preventing from chemical changes and physical phase-separation. Then the solution was finally mixed with antibiotic fruit juices and antifebrile vegetable juices, followed by stirring to obtain the growth supplement. More preferably, the cooling temperature is in the range of 35 to 40° C., because if the temperature of solution is too low, stirring process may become too difficult to conduct due to solubility property of increase in viscosity.

The growth supplement was prepared by using antibiotic fruit juice in an amount of 2 to 10 parts by weight; the source of hydrogen carbonate in an amount of 1 to 4 parts by weight; the source of chloride ion in an amount of 1 to 4 parts by weight; and antifebrile vegetable juice in an amount of 2 to 8 parts by weight, based on 100 parts by the source of sugar, and all the components used herein were commercially available products.

The growth supplement thus prepared was diluted with drinking water to give to livestock, and fed ad libitum. The dilution ratio of drinking water may vary depending on depending on species, age and livestock conditions, and the growth supplement was diluted with drinking water in an amount of 0.33 to 1.5 parts by weight, based on 100 parts by weight of water in Example. The amount used was expressed in parts by weight because the amount of the growth supplement required for dilution changes as the amount of drinking water varies.

Hereinafter, the effectiveness of the growth supplement on livestock and plants are described in more detail. First, the results of the growth supplement on livestock are described.

A clinical study was conducted on monogastric animal including pigs, ruminant animal including Hanwoo steers, and poultry including broiler chickens, Pekin ducks, Mallard ducks, and the like. In the livestock experiment, components, content ratio, dilution ratio and feeding amounts of the growth supplement in crude liquid were regulated depending on the species, age and livestock conditions. Test group and Control each had the same number of subjects, and the same livestock conditions were applied to each group, except for the use of the growth supplement. The test period was from the date of arrival of livestock until the date of shipment for all species. The measurement of the growth supplement amount ingested was taken daily. The average weight gain was measured by comparing the total weight of each group on the date of arrival with the total weight of each group on the date of shipment, except for poultry whose average weight was taken by selecting 10 average-sized subjects and measuring their weights every week.

Figure 3:
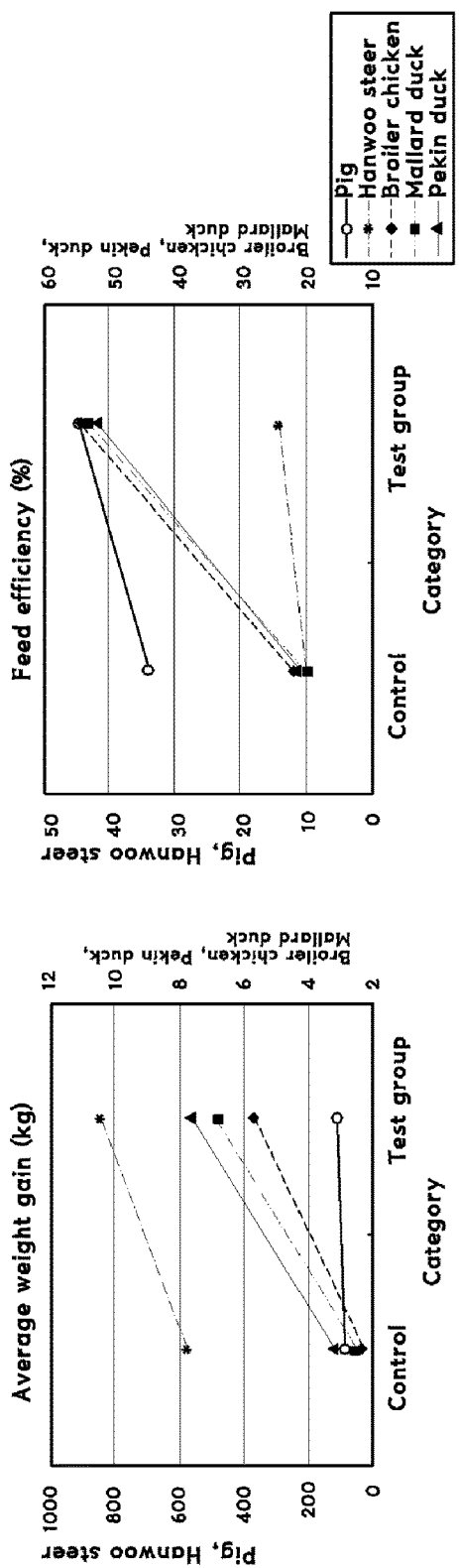
FIG. 3 is a graph demonstrating the average weight gain in various livestock fed on the growth supplement in accordance with one embodiment of the present invention and efficiency thereof as feedstuff.

Tables 2 and 3, and FIG. 3 show the comparison of test conditions, weight changes, etc. obtained from Test group fed on the growth supplement in accordance with the present invention, and Control group.

TABLE 2

| Species | Test Period | No. of subjects | | Amount of feed ingested (kg/subject) | | Average weight (g, kg) | | | Note |
| --- | --- | --- | --- | --- | --- | --- | --- | --- | --- |
| | | Test group | Control | Test group | Control | Before | After Test group | Control | |
| Broiler chicken | 85 days | 100 | 100 | 11 | 12 | 50 g | 6.2 | 2.9 | |
| Mallard duck | 85 days | 100 | 100 | 13 | 13 | 55 g | 7.3 | 3.1 | |
| Pekin duck | 85 days | 100 | 100 | 15 | 15 | 55 g | 8.2 | 3.8 | |
| Pig | 4 months | 50 | 50 | 250 | 250 | 30 | 141 | 115 | |
| Hanwoo steer | 24 months | 10 | 10 | 6000 | 6000 | 180 | 1020 | 752 | |

Table 2 shows the test conditions and changes in weight thereof for each species.

As shown in the Table 2, it can be concluded that the average weight gain and feed efficiency in Test group was superior to those of Control group. Particularly, the average weight gain in small poultry, i.e., broiler chickens, Mallard ducks and Pekin ducks, was superior to those of large-sized livestock, i.e., pigs and Hanwoo steers.

TABLE 3

| Species | *1) Growth rate | | *2) Average weight gain | | *3) Weight gain ratio | *4) Feed efficiency | | *5) Feed efficiency ratio | Note |
| --- | --- | --- | --- | --- | --- | --- | --- | --- | --- |
| | Test group | Control | Test group | Control | | Test group | Control | | |
| Broiler chicken | 11.4 | 4.8 | 5.7 | 2.4 | 2.4 | 54 | 21 | 2.6 | |
| Mallard duck | 12.3 | 4.6 | 6.8 | 2.6 | 2.6 | 53 | 19 | 2.7 | |
| Pekin duck | 13.9 | 5.9 | 7.7 | 3.3 | 2.4 | 52 | 22 | 2.4 | |
| Pig | 3.7 | 2.8 | 111 | 85 | 1.3 | 44 | 34 | 1.3 | |
| Hanwoo steer | 4.7 | 3.2 | 840 | 572 | 1.5 | 14 | 10 | 1.5 | |

TABLE 3-continued

| | *1) Growth rate | | *2) Average weight gain | | *3) Weight gain ratio | *4) Feed efficiency | | *5) Feed efficiency ratio | Note |
|---|---|---|---|---|---|---|---|---|---|
| Species | Test group | Control | Test group | Control | | Test group | Control | | |

*1) $\text{Growth rate} = \dfrac{(\text{average weight before test} - \text{average weight after test})}{\text{average weight before test}}$

*2) Average weight gain = average weight after test − average weight before test

*3) $\text{Weight gain ratio} = \dfrac{\text{average weight gain in Test group}}{\text{average weight gain in Control}}$

*4) Feed efficiency = (average weight gain/amount of feed ingested) × 100

*5) $\text{Feed efficiency ratio} = \dfrac{\text{feed efficiency in Test group}}{\text{feed efficiency in Control}}$ Table 3 shows the average weight gain, weight gain ratio, feed efficiency and feed efficiency ratio of each species.

With reference to Table 3, the weight gain ratio and the feed efficiency ratio of Test group to Control were 1.3 to 2.6 and 1.3 to 2.7, respectively. Thus, it can be confirmed that the weight gain ratio and the feed efficiency ratio were significantly enhanced. Particularly, the weight gain ratio and the feed efficiency ratio of broiler chickens and ducks came out to be 2.4 to 2.6 and 2.4 to 2.7, respectively. Whereas, the weight gain ratio and the feed efficiency ratio of large-sized animals, i.e., pigs and Hanwoo steers, were 1.3 to 1.5 and 1.3 to 1.5, respectively.

In sum, as can be seen in FIG. 3, subjects in Test group fed on the growth supplement demonstrated a noticeable increase in weight gain and feed efficiency as compared to Control group, which indicates that the growth supplement greatly improved livestock productivity. The effectiveness of the growth supplement was much greater in small-sized animals such as poultry, than in large-sized animals. Additionally, there was a large deviation between superior and inferior animals, which indicates there was an unequal distribution of weight among animals within the same species in Control group. In Test group, however, distribution of weight was even among subjects. Based on the above results, it can be concluded that not only superior animals can grow healthy by feeding on the growth supplement of the present invention, but also inferior, underweighted animals can grow healthy owing to the growth supplementary effect of the present invention.

Hereinafter, the effectiveness of the growth supplement on plants is described in more detail with reference to Table 4 and FIG. 4.

In the plant experiment, components, content ratio, dilution ratio of the growth supplement in crude liquid were fixed, and feeding amounts were regulated depending on the type of plant. In a similar manner to the animal experiment, Test group and Control each had the same size of cultivation area, and the same cultivation conditions were applied to each group, except for the use of the growth supplement.

Types of vegetable used in this experiment were green vegetable and fruit-vegetable: oak leaf lettuce, *Lactuca sativa* var. *crispa*, (hereinafter referred to as "leaf lettuce") was used as a green vegetable, and regular cherry tomato was used as a fruit-vegetable. Both groups were cultivated in a facility equipped with suitable water supply and drain system from the date of seeding until the date of shipment, and the growth supplement was applied to Test group only until the date of shipment.

Once vegetables have grown for a certain period of time, grown vegetables are harvested for shipment; and the period available for shipment (hereinafter referred to as "PAS") directly affects the total amount of vegetable produced, and thus the PAS plays an important role in productivity assessment. Unlike livestock, vegetable population is greater in number, and therefore, the total amounts produced in each of Test group and Control during the test period was added up, and the production ratios were calculated along with the growth ratio.

TABLE 4

| | Test area (3.3 m²) | | Test period (day) | Start of shipment (after seeding, day) | | PAS (day) | | *1)Group with ratio | Total amount produced (kg) | | *2)Production ratio |
|---|---|---|---|---|---|---|---|---|---|---|---|
| Crop type | Test group | Control | | Test group | Control | Test group | Control | | Test group | Control | |
| Leaf lettuce | 10 | 10 | 80 | 13 | 21 | 67 | 59 | 1.14 | 130 | 80 | 1.63 |
| Cherry tomato | 10 | 10 | 85 | 33 | 40 | 52 | 45 | 1.16 | 500 | 300 | 1.67 |

*1) $\text{Growth rate} = \dfrac{\text{average weight before test} - \text{average weight after test}}{\text{average weight before test}}$

*2) $\text{Production ratio} = \dfrac{\text{total amount produced in Test group}}{\text{total amount produced in Control}}$ Table 4 shows cultivation conditions of vegetables, growth ratio and production ratio.

As a result of feeding the growth supplement to the green vegetable, leaf lettuce, and the fruit-vegetable, tomato, the growth ratio and the production ratio of Test group to Control came out to be 1.14 to 1.16 and 1.63 to 1.67, respectively. This result was due to increased supply of nutrients required for growth, which increased PAS by shortening the time needed from seeding until start of shipment, and thus the vegetable can grow more rapidly, resulting in a substantial increase in the total amount produced.

Based on the result above, the growth supplement in accordance to the present invention can supply nutrients required for growth in green vegetable and fruit-vegetable to stimulate their rapid growth, therefore it can be confirmed that the production amount was significantly increased owing to rapid growth and extended PAS.

Figure 4:
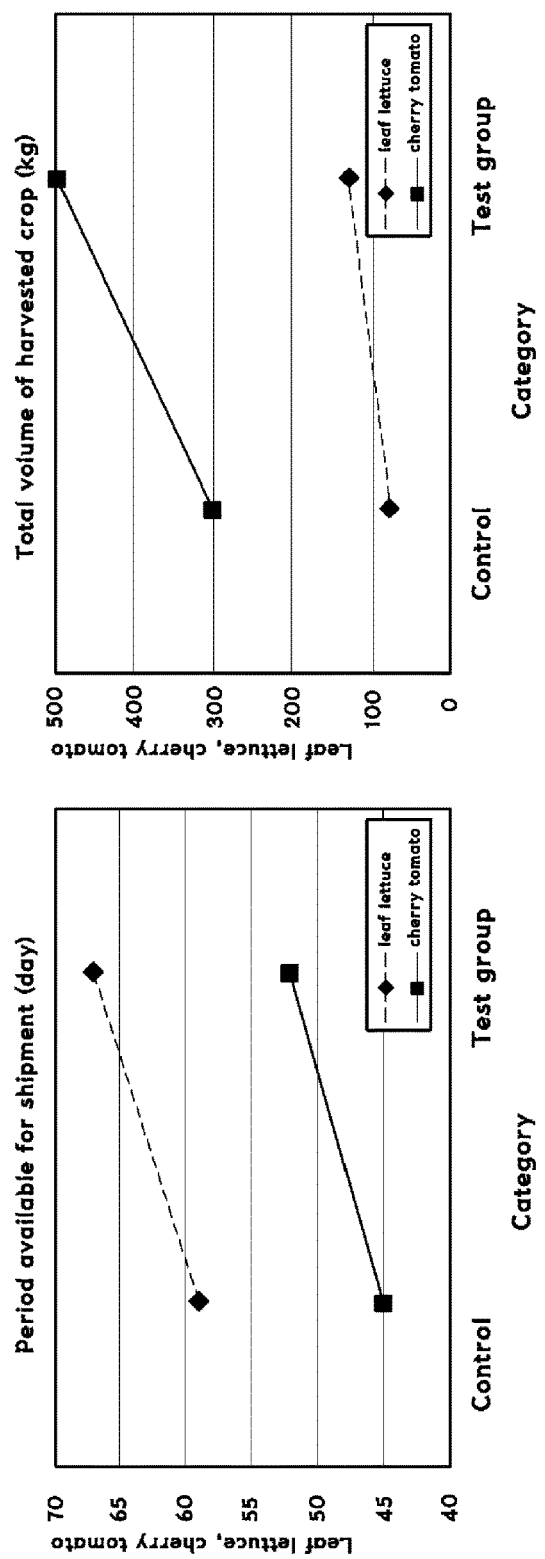
FIG. 4 is a graph showing the time required to harvest for various plants fed on one embodiment of the present invention and the total volume of harvested crops thereof.

As can be seen from the results of the experiment using the present invention on plants and livestock, with reference to FIG. 4, it can be confirmed that the present invention not only allows environment-friendly crop cultivation and livestock rearing, but also accelerates growth rate, which reduces time required to grow vegetable thereby increasing total yield, and enhances weight gain ratio and feed efficiency in livestock; and therefore, the present invention allows efficient production of environment-friendly agricultural and livestock products on a large scale.

While the invention has been described with respect to the above specific embodiments, it should be recognized that various modifications and changes may be made to the invention by those skilled in the art which also fall within the scope of the invention as defined by the appended claims.

What is claimed is:

1. A growth supplement for crops and livestock, comprising:
    glucose;
    one or more sources of hydrogen carbonate, wherein the source of hydrogen carbonate is one or more selected from the group consisting of sodium hydrogen carbonate and potassium hydrogen carbonate;
    one or more sources of chloride ion, wherein the source of chloride ion is one or more selected from the group consisting of sodium chloride, potassium chloride, magnesium chloride, and calcium chloride;
    antibiotic fruit juices, wherein the antibiotic fruit juices are one or more selected from the group consisting of schizandra fruit juice, jujube juice, red ginseng juice, and blueberry juice, wherein the antibiotic fruit juices enhance immune responses in the crops and the livestock; and
    one or more vegetable juices, wherein the vegetable juices are one or more selected from the group consisting of onion juice and dandelion juice;
    wherein based on 100 parts by weight of glucose, the growth supplement has,
    the source of the hydrogen carbonate in an amount of 1 to 4 parts by weight,
    the source of the chloride ion in an amount of 1 to 4 parts by weight,
    the antibiotic fruit juices in an amount of 2 to 10 parts by weight, and
    the vegetable juices in an amount of 2 to 8 parts by weight.

2. The growth supplement of claim 1, wherein the source of hydrogen carbonate is sodium hydrogen carbonate.

3. The growth supplement of claim 1, wherein the source of chloride ion is potassium chloride.

4. A growth supplement according to claim 1, wherein the growth supplement is prepared by diluting with water or adding to feedstuff.

5. A growth supplement according to claim 2, wherein the growth supplement is prepared by diluting with water or adding to feedstuff.

6. A growth supplement according to claim 3, wherein the growth supplement is prepared by diluting with water or adding to feedstuff.

* * * * *